United States Patent
Dobson

(10) Patent No.: US 10,251,905 B2
(45) Date of Patent: Apr. 9, 2019

(54) TISSUE MAINTENANCE

(71) Applicant: Hibernation Therapeutics, A KF LLC, Camden, DE (US)

(72) Inventor: Geoffrey Phillip Dobson, Wulguru (AU)

(73) Assignee: HIBERNATION THERAPEUTICS, A KF LLC, Camden, DE (US)

( * ) Notice: Subject to any disclaimer, the term of this patent is extended or adjusted under 35 U.S.C. 154(b) by 1232 days.

(21) Appl. No.: 13/899,060

(22) Filed: May 21, 2013

(65) Prior Publication Data

US 2014/0005137 A1 Jan. 2, 2014

Related U.S. Application Data

(63) Continuation of application No. 13/337,621, filed on Dec. 27, 2011, now abandoned, which is a continuation of application No. 12/303,058, filed as application No. PCT/AU2006/000717 on May 29, 2006, now abandoned.

(51) Int. Cl.
| | |
|---|---|
| A01N 59/00 | (2006.01) |
| A61K 31/7076 | (2006.01) |
| A61K 31/167 | (2006.01) |
| A61K 33/06 | (2006.01) |
| A61K 45/06 | (2006.01) |
| A01N 1/02 | (2006.01) |

(52) U.S. Cl.
CPC ........ *A61K 31/7076* (2013.01); *A01N 1/0226* (2013.01); *A61K 31/167* (2013.01); *A61K 33/06* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,798,824 A | 1/1989 | Belzer et al. | |
| 5,006,512 A | 4/1991 | Ohnishi | |
| 5,145,771 A | 9/1992 | Lemasters et al. | |
| 5,206,222 A | 4/1993 | Forman et al. | |
| 5,256,770 A | 10/1993 | Glaser et al. | |
| 5,370,989 A | 12/1994 | Stern et al. | |
| 5,407,793 A | 4/1995 | Del Nido | |
| 5,432,053 A | 7/1995 | Berdyaev et al. | |
| 5,514,536 A | 5/1996 | Taylor | |
| 5,656,420 A | 8/1997 | Chien | |
| 5,679,706 A | 10/1997 | D'Alonzo et al. | |
| 5,693,462 A | 12/1997 | Raymond | |
| 6,011,017 A | 1/2000 | Marangos et al. | |
| 6,187,615 B1 | 2/2001 | Kim et al. | |
| 6,187,756 B1 | 2/2001 | Lee et al. | |
| 6,358,208 B1 | 3/2002 | Lang et al. | |
| 6,372,723 B1 | 4/2002 | Martin et al. | |
| 6,569,615 B1 | 5/2003 | Thatte et al. | |
| 6,586,413 B2 | 7/2003 | Liang et al. | |
| 6,921,633 B2 | 7/2005 | Baust et al. | |
| 6,955,814 B1 | 10/2005 | Dobson | |
| 6,992,075 B2 | 1/2006 | Hill et al. | |
| 7,223,413 B2 | 5/2007 | Dobson | |
| 7,749,522 B2 | 7/2010 | Dobson | |
| 2001/0041688 A1 | 11/2001 | Waeber et al. | |
| 2003/0216775 A1 | 11/2003 | Hill et al. | |
| 2004/0229780 A1 | 11/2004 | Olivera | |
| 2005/0176763 A1 | 8/2005 | Boy et al. | |
| 2006/0034941 A1 | 2/2006 | Dobson | |
| 2009/0198145 A1 | 8/2009 | Chow | |
| 2013/0122108 A1 | 5/2013 | Matheny | |

FOREIGN PATENT DOCUMENTS

| | | | |
|---|---|---|---|
| CN | 1176738 A | 3/1998 | |
| CN | 1057192 | 10/2000 | |
| CN | 101019529 | 8/2007 | |
| CN | 101496512 A | 8/2009 | |
| CN | 102726366 A | 10/2012 | |
| DE | 39 26287 | 2/1991 | |
| GB | 2 436 255 A | 9/2007 | |
| JP | 09-151134 | 6/1997 | |
| SU | 0878297 | 11/1981 | |
| WO | WO-92/20346 A1 | 11/1992 | |
| WO | WO-98/37886 | 9/1998 | |
| WO | WO-00/03716 A1 | 1/2000 | |
| WO | WO-00/24378 A1 | 5/2000 | |
| WO | WO-00/056145 A1 | 9/2000 | |
| WO | WO2000/56145 | * 9/2000 | ............... A61K 9/00 |
| WO | WO-2001/045684 | 6/2001 | |
| WO | WO-01/54679 A2 | 8/2001 | |
| WO | WO-01/82914 A2 | 11/2001 | |
| WO | WO-03/063782 A2 | 8/2003 | |
| WO | WO-03/088978 A1 | 10/2003 | |
| WO | WO-2004/000331 A1 | 12/2003 | |
| WO | WO-2004/000331 A1 | 12/2003 | |
| WO | WO-04/056180 | 7/2004 | |
| WO | WO-04/056181 A1 | 7/2004 | |
| WO | WO-04/060286 | 7/2004 | |
| WO | WO-2004/056180 A1 | 7/2004 | |
| WO | WO-2004/056181 A1 | 7/2004 | |
| WO | WO-2004/060286 A2 | 7/2004 | |
| WO | WO-04/108666 A2 | 12/2004 | |
| WO | WO-2004/108666 A2 | 12/2004 | |
| WO | WO-2006/069170 A2 | 6/2006 | |
| WO | WO-2007/030198 A2 | 3/2007 | |
| WO | WO-2007/030198 A2 | 3/2007 | |
| WO | WO-2007/137321 A1 | 12/2007 | |
| WO | WO-08/011670 A1 | 1/2008 | |
| WO | WO-2008/011670 A1 | 1/2008 | |
| WO | WO-2008/040094 A1 | 4/2008 | |
| WO | WO-08/106724 A1 | 9/2008 | |
| WO | WO-2008/106724 A1 | 9/2008 | |
| WO | WO-09/012534 A1 | 1/2009 | |
| WO | WO-2009/012534 A1 | 1/2009 | |
| WO | WO-2011/075391 A1 | 6/2011 | |

OTHER PUBLICATIONS

Gao et al. Journal of Huazhong University of Science and Technology [Med Sci]. 2003; 23(4): 407-410.*

(Continued)

*Primary Examiner* — David Browe
(74) *Attorney, Agent, or Firm* — Keith G. Haddaway; Miguel A. Lopez; Venable LLP

(57) ABSTRACT

The invention provides a method of reducing damage to a tissue, organ or cell from surgical procedures comprising administering a composition comprising a potassium channel opener/agonist and/or an adenosine receptor agonist (eg. adenosine) together with a local anaesthetic (eg. lignocaine) when perfusing the organ.

16 Claims, No Drawings

(56) References Cited

OTHER PUBLICATIONS

Takeuchi et al. Ann. Thorac. Surgery. 1999; 68: 903-907.*
Thourani et al., "Myocardial Protection with Adenosine Given at Reperfusion is Superior to Adenosine-Enhanced Cardioplegia," Insulin Cardioplegia for Coronary Bypass Surgery, Supplement I, 3217, pp. 1-2.
Thourani et al., "Adenosine-Supplemented Blood Cardioplegia Attenuates Postischemic Dysfunction After Severe Regional Ischemia," Circulation, 1999, pp. II-376-II-383.
Ar-Rajab et al. "Improved Liver Preservation for Transplantation Due to Calcium Channel Blockade", Transplantation, 51(5):965-967, May 1991.
Beyersdorf, F, "The use of controlled reperfusion strategies in cardiac surgery to minimize ischaemia/reperfusion damage," *Cardiovascular Research*, 83, 262-268, 2009.
Brett et al., "Evolutionary origins of eukaryotic sodium/proton exchangers," Am. J. Phsysiol. Cell Physiol. 288: C223-C239, 2005.
Canyon et al. "The Effect of Adenosine and Lidocaine Infusion on Myocardial High-Energy Phosphates and pH During Regional Ischemia in the Rat Model in vivo", Canadian Journal of Physiology and Pharmacology, vol. 84, 903-912, Oct. 18, 2006.
Canyon et al., "Pretreatment with an Adenosine A1 Receptor Agonist and Lidocaine: A Possible Alternative to Myocardial Ischemic Preconditioning," The Journal of Thoracic and Cardiovascular Surgery, vol. 130, No. 2, pp. 371-377, 2005.
Canyon et al., "Protection Against Ventricular Arrhythmias and Cardiac Death Using Adenosine and Lidcaine During Regional Ischemia in the In Vivo Rat," Am J. Physiol Heart Circ Physiol 287:H1286-H1295; American Physiological Society 2004.
Chien et al., "Extension of Tissue Survival Time in Multiorgan Block Preparation With a Delta Opioid DADLE (D-Ala$^2$, D-Leu$^5$)-enkephalin)," Thoracic and Cardiovascular Surgery, 107:965-967, 1994.
Corvera et al., "Polarised Arrest With Warm or Cold Adenosine/Lidocaine Blood Cardioplegia is Equivalent to Hypothermic Potassium Blood Cardioplegia", The Journal of Thoracic and Cardiovascular Surgery, 129(3):599-606, May 2005.
Das et al., 2002 Myocardial preservation during cardiac surgery, Annals of Cardiac Anaesthesia, vol. 5, pp. 25-32.
Derwent Abstract Account No. 74319 E/35; SU 878297 A, 1981.
Dobson et al., "Adenosine and Lidocaine: A New Concept in Nondepolarizing Surgical Myocardial Arrest, Protection and Preservation," The Journal of Thoracic and Cardiovascular Surgery 127:794-805, Mar. 2004.
Dobson GP, Membrane polarity: A target fro myocardial protection and reduced inflammation in adult and pediatric cardiothoracic surgery, The Journal of Thoracic and Cardiovascular Surgery, vol. 140, No. 6, pp. 1213-1217, 2010.
Dobson, "Organ Arrest, Protection and Preservation: Natural Hibernation to Cardiac Surgery," Comparative Biochemistry and Physiology, Part B 139:469-485 Elsevier Inc., 2004.
Dobson, Geoffrey, "Bloody Battle" Australian Science, pp. 14-16, 2011.
Ely, S.W. et al. "Protective Effects of Adenosine in Myocardial Ischemia", Circulation, 85(3): 893-904, Mar. 1992.
Forman et al. "Mechanisms and Therapy of Myocardial Reperfusion Injury". Circulation, 81(3 Suppl):IV69-78, Mar. 1990.
Forman et al., "Adenosine Therapy at Reperfusion on Myocardial Infarct Size," Cardiovascular Research, 33:497-498, 1997.
Garratt et al., "Intravenous Adenosine and Lidocaine in Patients with Acute Myocardial Infarction," American Heart Journal, 136(2):196-204, Aug. 1998.
Goto et al. "Adenosine Infusion During Early Reperfusion Failed to Limit Myocardial Infarct Size in a Collateral Deficient Species" Cardiovascular Research, 25(11):943-9, Nov. 1991.
Granger, C.B. "Adenosine for Myocardial Protection in Acute Myocardial Infarction", The American Journal of Cardiology, 79(12A): 44-48, Jun. 1997.
Granger, C.B., "Adenosine and Lidocaine: A New Concept in Nondepolarizing Surgical Myocardial Arrest, Protection and Preservation", The Journal of Thoracic and Cardiovascular Surgery 127:794-805, Jun. 1997.
Hearse et al., "Protection of the Myocardium during ischemic arrest," J. Thorac. Cardiovasc. Surg., vol. 81, No. 6, pp. 873-879, 1981.
Hicks, et al., "ATP-Sensitive Potassium Channel Activiation Mimics the Protective Effect of Ischaemic Preconditioning in the Rat Isolated Working Heart After Prolonged Hypothermic Storage," Clinical and Experimental Pharmacology and Physiology 26:20-25, 1999.
Homeister et al., "Combined Adenosine and Lidocaine Administration Limits Myocardial Reperfusion Injury," Circulation, 82(2):595-608, Aug. 1990.
Huang, T. F., "Drug Effects on the lschemia- and Reperfusion-induced Arrhythmias in the Conscious Rats", Chinese Journal of Physiology 35(1): 9-19, 1992.
International Application Status Report, Dated Dec. 21, 2009, issued in related International Application No. PCT/AU2007/001029.
International Preliminary Examination Report, dated Mar. 5, 2001, issued in related International Application No. PCT/AU00/00226.
International Preliminary Examination Report, dated Oct. 12, 2004, issued in related International Application No. PCT/AU2003/000771.
International Preliminary Report on Patentability and Written Opinion, dated Dec. 3, 2008, issued in related International Application No. PCT/AU2006/000717.
International Preliminary Report on Patentability and Written Opinion, dated Jan. 27, 2009, issued in related International Application No. PCT/AU2007/001029.
International Preliminary Report on Patentability and Written Opinion, dated Sep. 8, 2009, issued in related International Application No. PCT/AU2008/000289.
International Search Report and Written Opinion dated Sep. 25, 2008, issued in related International Application No. PCT/AU2008/001086.
International Search Report dated Aug. 4, 2003, issued in related International Application No. PCT/AU03/00771.
International Search Report dated Feb. 13, 2004, issued in related International Application No. PCT/AU2003/001711.
International Search Report dated Jul. 21, 2006, issued in related International Application No. PCT/AU2006/000717.
International Search Report dated Jun. 9, 2000, issued in related International Application No. PCT/AU00/00226.
International Search Report Issued in PCT/AU2007/001029 dated Sep. 25, 2007.
International Search Report, dated May 7, 2008, issued in related International Application No. PCT/AU2008/000289.
Jakosben et al., Adenosine instead of supranormal potassium in cardioplegic solution improves cardioprotection, European Journal of Cardio-thoracic Surgery, vol. 32, pp. 493-500, 2007.
Jakosben et al., Adenosine instead of supranormal potassium in cardioplegic solution preserves endothelium-derived hyperpolarization factor-dependent vasodilation, European Journal of Cardio-thoracic Surgery, vol. 33, pp. 18-24, 2008.
Jayawant et al., "Advantages of Continuous Hyperpolarized Arrest with Pinacidil Over St. Thomas' Hospital Solution During Prolonged Ischemia," J. Thoracic and Cardiovascular Surgery, 11(1):131-138, 1998.
Jayawant, AM et al "Potassium-channel opener cardioplegia is superior to St. Thomas' solution in the intact animal," *Ann Thorac Surg*, 68, 67-74, 1999.
Jin et al, 2008 The myocardial protective effects of a moderate-potassium adenosine-lidocaine cardioplegia in pediatric cardiac surgery, The Journal of Thoracic and Cardiovascular Surgery, vol. 136, No. 6, pp. 1450-1455.
Karck et al, "Myocardial protection by ischemic preconditioning and δ-opioid receptor activiation in the isolated working rat heart," *The Journal of Thoracic and Cardiovascular Surgery*, 122, 986-992, 2001.

(56) References Cited

OTHER PUBLICATIONS

Kinoshita et al, "Mild alkalinisation and acidification deifferentially modify the effects of lidocaine or mexiletine on vasorelaxation mediated by ATP-sensitive K+ channels" *Anesthesiology*, 95, 200-206, 2001.

Kusano T. et al., "Organ Preserving Effect of lidocaine Administration in the Model of Orthopic Liver Transplantation from Non-heart Beating Donors", Transplantation Proceedings, 28(3):1928-1929, Jun. 1996.

Lee et al., "Retrograde infusion of liocaine or L-arginine before reperfusion reduces myocardial infarct size", Ann. Thorac. Surg 65:1353-1359.

Mahaffey et al., "Adenosine as an Adjunct to Thrombolytic Therapy for Acute Myocardial Infarction," JACC 34(6):1711-20, Nov. 1999.

Neely et al., "A1 Adenosine Receptor Antagonist Block Ischemia-reperfusion Injury of the Heart", Circulation, Supplement 94(9):11376-11380, 1996, abstract.

O'Rullian et al., Excellent Outcomes in a Case of complex Re-do Surgery Requiring Prolonged Cardioplegia Using a New Cardioprotective Approach: Adenocaine, The Journal of ExtraCorporeal Technology, vol. 40, pp. 203-205, 2008.

Rudd et al. "Toward a New Cold and Warm Nondepolarizing, Normokalemic Arrest Paradigm for Orthotopic Heart Transplantation", Journal of Thoracic and Cardiovascular Surgery, 137(1):198-207, Jan. 2009.

Rudd et al., Early reperfusion with warm, polarizing adenosine-lidocaine cardoplegia improves functional recovery after 6 hours of cold static storage, The Journal of Thoracic and Cardiovascular Surgery, vol. 141, No. 4, pp. 1044-1055, 2011.

Schubert et al., "Adenosine cardioplegia," J. Thorac. Cardiovasc. Surg., vol. 98, No. 6, pp. 1057-1065, 1989.

Segal et al., "On the Natriuretic Effect of Verapamil: Inhibition of EnaC and Transephithelial Sodium Transport", *Am J. Physiol Renal Physiol*, 283: F765-F770, 2002.

Sloots et al, 2007 Warmnondepolarizing adenosine and lidocaine cardioplegia: Continuous versus intermittent delivery, The Journal of Thoracic and Cardiovascular Surgery, vol. 133, No. 5, pp. 1171-1178.

STN File CAplus Abstact 147:317797.

STN File CAplus Abstract 132:242003.

Su, T-P., "Delta Opioid Peptide [D-Ala2, D-Leu5] Enkephalin Promotes Cell Survival," J. Biomed. Sci., 7:195-199, 2000.

Sultan et al., "Heart Preservation: Analysis of Cardioprotective Infusate Characteristics, Membrane Stabilization, Calcium Antagonism, and Protease Inhibition on Myocardial Viability: A Biochemical, Ultrastructural, Functional Study," The Journal of Heart and Lung Transplantation 11(4):607-18, 1992.

Supplementary European Search Report dated Jun. 10, 2002, issued in related European Patent Application No. EP 00 91 0414.

Takeuchi et al. "Prolonged Preservation of the Blood-Perfused Canine Heart with Glycolysis-Promoting Solution," Ann Thorac Surgery 68:903-7, 1999.

Ulusal et al., "The Effect of A2a Adenosine Receptor Agonist on Composite Tissue Allotransplant Survival: An In Vitro Preliminary Study", J. Surgical Research 131: 261-266, 2006.

Vander Heide et al., "Adenosine Therapy at Reperfusion and Myocardial Infarct Size," Cardiovascular Research, 33:499-500, 1997.

Brett, CL et al., "Evolutionary origins of eukaryotic sodium/proton exchangers" *Am J Physiol Cell Physiol*, 288, C223-C239 (2005).

Canyon, SJ, et al., "Protection Against Ventricular Arrhythmias and Cardiac Death Using Adenosine and Lidcaine During Regional Ischemia in the In Vivo Rat," *Am J. Physiol Heart Circ Physiol* 287:H1286-H1295; American Physiological Society 2004.

Canyon, SJ, et al., "Pretreatment with an Adenosine A1 Receptor Agonist and Lidocaine: A Possible Alternative to Myocardial Ischemic Preconditioning," The Journal of Thoracic and Cardiovascular Surgery, vol. 130, No. 2, pp. 371-377, 2005.

Canyon, SJ, et al., "The Effect of Adenosine and Lidocaine Infusion on Myocardial High-Energy Phosphates and pH During Regional Ischemia in the Rat Model in vivo", Canadian Journal of Physiology and Pharmacology, vol. 84, 903-912, Oct. 18, 2006.

Chien, S, et al., "Extension of Tissue Survival Time in Multiorgan Block Preparation With a Delta Opioid DADLE (D-Ala2, D-Leu5)-enkephalin)," The Journal of Thoracic and Cardiovascular Surgery, 107:965967, 1994.

Corvera, JS, et al., "Polarised Arrest With Warm or Cold Adenosine/Lidocaine Blood Cardioplegia is Equivalent to Hypothermic Potassium Blood Cardioplegia," *The Journal of Thoracic and Cardiovascular Surgery*, 129(3):599-606, May 2005.

Das, et al., "Myocardial preservation during cardiac surgery", *Annals of Cardiac Anaesthesia*, vol. 5, pp. 25-32, 2002.

Dobson, G.P., "Organ Arrest, Protection and Preservation: Natural Hibernation to Cardiac Surgery," Comparative Biochemistry and Physiology, 139 (Part B):469-485; Elsevier Inc., 2004.

Dobson, G.P., et al., "Adenosine and Lidocaine: A New Concept in Nondepolarizing Surgical Myocardial Arrest, Protection and Preservation," The Journal of Thoracic and Cardiovascular Surgery 127:794-805, Mar. 2004.

Ely, S.W., et al., "Protective Effects of Adenosine in Myocardial Ischemia", Circulation, 85(3): 85(3):893-904, Mar. 1992.

Huang, T.F., "Drug Effects on the Ischemia- and Reperfusion-induced Arrhythmias in the Conscious Rats", Chinese Journal of Physiology 35(1): 9-19,1992.

International Preliminary Report on Patentability, dated Dec. 3, 2008, issued in related Internatibnal Application No. PCT/AU2006/000717.

International Preliminary Report on Patentability, dated Jan. 27, 2009, issued in related International Application No. PCT/AU2007/001029.

International Preliminary Report on Patentability, dated Sep. 8, 2009, issued in related International Application No. PCT/AU2008/000289.

International Preliminary Report on Patentability, dated Jan. 26, 2010, issued in related International Application No. PCT/AU2008/001086.

International Search Report dated Feb. 13, 2004, issued in related International Application No. PCT/AU2003/001710.

International Status Report, Dated Sep. 25, 2007, issued in related International Application No. PCT/AU2007/001029.

International Search Report dated Sep. 25, 2008, issued in related International Application No. PCT/AU2008/001086.

Jin, et al, "The myocardial protective effects of a moderate-potassium adenosine-lidocaine cardioplegia in pediatric cardiac surgery", The Journal of Thoracic and Cardiovascular Surgery, vol. 136, No. 6, pp. 1450-1455, 2008.

Karck, M., et al, "Myocardial protection by ischemic preconditioning and -opioid receptor activiation in the isolated working rat heart" The Journal of Thoracic and Cardiovascular Surgery, 122, 986-992 (2001).

Kinoshita, H., et al "Mild alkalinisation and acidification deifferentially modify the effects of lidocaine or mexiletine on vasorelaxation mediated by ATP-sensitive K+ channels" Anesthesiology, 95, 200-206 (2001).

Lee et al., "Retrograde infusion of liocaine or L-arginine before reperfusion reduces myocardial infarct size", Ann. Thorac. Surg 65:1353-1359, 1998.

Rogriguez-Reynoso, et al "Effect of exogenous melatonin on hepatic energetic status during ischemia/reperfusion: possible role of tumor necrosis factor-a and nitric oxide" *J Surgical Research*, 100(2), 141-149 (2001).

Rudd, DM, et al. "Toward a New Cold and Warm Nondepolarizing, Normokalemic Arrest Paradigm for Orthotopic Heart Transplantation", Journal of Thoracic and Cardiovascular Surgery, 137(1): 198-207, Jan. 2009.

Sigg, et al "Role of d-opioid receptor agonists on infarct size reduction in swine" Am. J. Physiol. Heart Circ. Physiol, 282, H1953-H1960 (2002).

(56) References Cited

OTHER PUBLICATIONS

Silber, et al "A rapid hemodynamic monitor of acute ischemia during cardiac procedures: changes in relaxation via a continuous left ventricular pressure-derivative loop" J Surg Res, 134(1), 107-113 (2006) with Medline entry Acc No. 2006367738.

Sloots, K, et al, "Warm nondepolarizing adenosine and lidocaine cardioplegia: Continuous versus intermittent delivery," The Journal of Thoracic and Cardiovascular Surgery, vol. 133, No. 5, pp. 1171-1178. 2007.

Ulusal, et al., "The Effect of A2a Adenosine Receptor Agonist on Composite Tissue Allotranspiant Survival: An In Vitro Preliminary Study", J. Surgical Research 131: 261-266, 2006.

Vinten-Johansen, J., et al. "Preconditioning and postconditioning: innate cardioprotection from ischemia-reperfusion injury." Journal of Applied Physiology, 103(4). pp. 1441-1448, 2007.

Wu, et al., "Mechanism of cardiac protection by preconditioning and postconditioning for hypoxia-reoxygenation injury is different" Jpn J Physiol, 54, S96, item 127 (2004).

Gross et al., "Opioids and myocardial reperfusion injury," Cardiovascular Research, Arch. Mal. Coeur. Vaiss 2007: 100: 231-2237.

McAllister et al., "Abstract 1419: Ischemic Postconditioning Against Ischemia/Reperfusion Injury Beyond the Myocardium," Circulation 2006: 114: 271.

Bryland et al "Citrate treatment reduces endothelial death and inflammation under hyperglycaemic conditions" Diabetes and Vascular Disease Research 9(1) 42-51 2011.

Djabir, Y, et al., "60 Minutes of Cardiac Rescue and Stabilization with a Small Intravenous Bolus of Adenocaine Following 8 Minutes of Asphyxial Hypoxia in the Rat in Vivo: Effect of Therapeutic Hypothermia." Circulation, 124 (21 Supplement). p. 1, 2011.

Djabir, Y, et al., "Adenosine, Lidocaine, and Mg2+ (ALM) Increases Survival and Corrects Coagulopathy After Eight-Minute Asphyxial Cardiac Arrest in the Rat." Shock, 40(3):222-32, Sep. 2013.

Dobson GP & Jones MW "Adenosine and Lignocaine: a New Concept in Cardiac Arrest and Preservation" Ann Thorac Surg 75 S746 (Abstract) 2003.

Dobson, G.P., "Small animal model species are not created equal." Critical Care Medicine, 40 (2). p. 711, 2012.

Dobson, G.P., "Hyperkalemic cardioplegia for adut and pediatric surgery: end of an era?", Front Physiol. Aug. 28;4:228. Review, 2013.

Dobson GP "Addressing the global burden of trauma in major surgery" Fontiers in Surgery 2(43) Sep. 1-26, 2015.

Dobson GP & Letson HL "Adenosine, lidocaine, and Mg2+ (ALM): From cardiac surgery to combat casualty care—Teaching old drugs new tricks" J Trauma Acute Care Surg 80(1) 135-145 2015.

Donohue DM et al "Erythrocyte Preservation. VI The storage of blood with purine nucleosides" Journal of Clinical Investigation 562-567 May 1956.

Fukihiro Y et al "Cardioplegic strategies for calcium control Low Ca2 , High Mg2 , Citrate, or Na /H Exchange Inhibitor HOE-642" Circulation 102:III319-III325 2000.

Giangrande PLF "The history of blood transfusion" British Journal of Haematology 110 758-767 2000.

Granfeldt, A., et al. "Resuscitation with adenocaine and magnesium reduces fluid requirement and improves cardiac function following 72% blood loss in the pig." Circulation 124 (21 Supplement). p. 1, 2011.

Granfeldt, A., et al., "Adenocaine and Mg2+ reduce fluid requirement to maintain hypotensive resuscitation and improve cardiac and renal function in a porcine model of severe hemorrhagic shock" Crit Care Med, 40(11), 3013-3025, (2012).

Hammon, JW, "Why change?", The Journal of Thoracic and Cardiovascular Surgery 140:1218-1219, 2010.

International Preliminary Report on Patentability, dated Jan. 19, 2016, issued in related International Application No. PCT/AU2014/050132.

International Preliminary Report on Patentability, dated Jan. 19, 2016, issued in related International Application No. PCT/AU2014/050128.

International Preliminary Report on Patentability, dated Jan. 19, 2016, issued in related International Application No. PCT/AU2014/050130.

International Preliminary Report on Patentability, dated Jan. 19, 2016, issued in related International Application No. PCT/AU2014/050131.

International Preliminary Report on Patentability, dated Jan. 19, 2016, issued in related International Application No. PCT/AU2014/050133.

International Search Report dated Sep. 25, 2014, issued in related International Application No. PCT/AU2014/050132.

International Search Report dated Sep. 10, 2014, issued in related International Application No. PCT/AU2014/050128.

International Search Report dated Sep. 24, 2014, issued in related International Application No. PCT/AU2014/050130.

International Search Report dated Sep. 16, 2014, issued in related International Application No. PCT/AU2014/050131.

International Search Report dated Sep. 16, 2014, issued in related International Application No. PCT/AU2014/050133.

Kato R et al "Fentanyl protects the heart against ischaemic injury via opioid receptors, adenosine A1 receptors and KATP channel linked mechanisms in rats" British Journal of Anaesthesia 84(2):204-14 2000.

Letson, H.L., & Dobson G.P. "Ultra-small intravenous bolous of 7.5% NaCl/Mg2+ with adenosine and lidocaine improves early rescusctation outcome in the rat after severe hemorrhagic shock in vivo." Journal of Trauma, 71(3). pp. 708-719, 2011.

Letson, H.L., & Dobson G.P, "Unexpected 100% survival following 60% blood loss using small-volume 7.5% NaCl with Adenocaine and Mg2+ in the rat model of extreme hemorrhagic shock." Shock, 36(6). pp. 586-594, 2011.

Letson, H.L., & Dobson G.P., "Small volume 7.5% NaCl with 6% dextran-70 or 6% and 10% hetastarch are associated with arrhythmias and death after 60 minutes of severe hemorrhagic shock in the rat in vivo." Journal of Trauma, 70(6), pp. 1444-1452, 2011.

Letson, H.L., et al. "Reversal of acute coagulopathy using small-volume 7.5% NaCl with adenocaine and Mg2+ resuscitation in a rat model of severe hemorrhagic shock." Circulation, 124 (21 Supplement). p. 1, 2011.

Letson, H.L., et al "Reversal of acute coagulopathy during hypotensive resuscitation using small-volume 7.5% NaCl adenocaine and Mg2+ in the rat model of severe hemorrhagic shock." Critical Care Medicine, 40(8). pp. 2417-2422, 2012.

Letson, H.L., & Dobson, G.P., "Acute coagulopathy of trauma in the rat." Shock 39: 440-446, 2013.

Morabito S et al "Regional citrate anticoagulation in cardiac surgery patients at high risk of bleeding: a continuous veno-venous hemofiltration protocol with a low concentration citrate solution" Critical Care 16:R111 2012.

Morabito S et al "Continuous venovenous hemodiafiltration with a low citrate dose regional anticoagulation protocol and a phosphate-containing solution: effects on acid-base status and phosphate supplementation needs" BMC Nephrology 14:232 2013.

Noera G "When and why CDP in continous warm blood cardioplegia?" Ann Thorac Surg 56:1214-20 1993.

O'Neill LAJ "A critical role in citrate metabolism in LPS signalling" Biochem J 439 e5-e6 2011.

Onorati F "Polarizing microplegia improves cardiac cycle efficiency after CABG for unstable angina" International Journal of Cardiology 167: 2739-2746 2013.

Patel NN et al "Phosphodiesterase-5 Inhibition Prevents Postcardiopulmonary Bypass Acute Kidney Injury in Swine" Ann Thorac Surg 92:2168-76 2011.

Rosenkranz ER & Buckberg GD "Myocardial protection during surgical coronary reperfusion" J Am Coll Cardiol 1(5)1235-46 1983.

Rudd, DM, et al., "Early reperfusion with warm, polarizing adenosine-lidocaine cardoplegia improves functional recovery after 6 hours of cold static storage," The Journal of Thoracic and Cardiovascular Surgery, vol. 141, No. 4, pp. 1044-1055, 2011.

(56) References Cited

OTHER PUBLICATIONS

Rudd, D.M., & Dobson, G.P., "Eight hours of cold static storage with adenosine and lidocaine (Adenocaine) heart preservation solutions: towards therapeutic suspended animation." Journal of Thoracic and Cardiovascular Surgery, 142(6). pp. 1552-1561, 2011.
Sawynok J et al "Antidepressants as analgesics: an overview of central and peripheral mechanisms of action" Journal of Psychiatry & Neuroscience 26(1): Jan. 21-29, 2001.
Shi "The novel non-depolarizing, normokalemic cardioplegia formulation based on the combination of adenosine-lidocaine (AdenocaineTM) exerts superior anti-neutrophil effects by synergistic actions of its components" FASEB J 1b548 (Abstract) 2010.
Shi, W, et al., "The nondepolarizing, normokalemic cardioplegia formulation adenosine-lidocain (adenocaine) exerts anti-neutrophil effects by synergistic actions of its components." The Journal of Thoracic and Cardiovascular Surgery, 143(5), pp. 1167-1175, 2012.
Sloots, K., & Dobson G., "Normokalemic adenosine-lidocaine cardioplegia: importance of maintaining a polarized myocardium for optimal arrest and reanimation." Journal of Thoracic and Cardiovascular Surgery, 139(6). pp. 1576-1586, 2010.
Vinten-Johansen J et al "Polarized arrest with adenosine-lidocaine blood cardioplegia: A new paradigm in myocardial protection" Journal of Molecular and Cellular Cardiology 35:A7 (Abstract) 2003.
Vinten-Johansen, J., & Dobson G.P., "Adenosine-procaine cardioplegia and adenosine-lidocaine cardioplegia: Two sides of the same coin?" J Thorac Cardiovasc Surg. Jun: 145(6):1684-5, 2013.
Vinten-Johansen, J., "Adenosine-lidocaine-magnesium non-depolarizing cardioplegia: Moving forward from bench to bedside" International Journal of Cardiology, (2012).
STN File CAplus Abstract 147:317797 (Abstract of CN1176728 (Zheng) 1998).
STN File CAplus Abstract 132:242003 (Abstract of CN101019529 (Sun) 2007).

\* cited by examiner

TISSUE MAINTENANCE

FIELD OF THE INVENTION

The invention relates to protecting and preserving tissue following disruptions to normal metabolite flow, such as may occur to the heart during cardioplegia. The invention also relates to a method for improving post-operative patient recovery following surgery. In particular, it has particular application to minimising post-operative complications following cardiac surgery, particularly following cardioplegia applied directly to the heart rather than systemically.

BACKGROUND OF THE INVENTION

Of the million elective open-heart surgeries performed globally each year, 1 to 3% of patients will die in the recovery room, 10% will leave the hospital with left ventricular dysfunction, up to 30% will experience atrial arrhythmias, and 24% of high risk patients will die within 3 years. Moreover, recent prospective studies have shown that patients with a slightly elevated post-operative creatine kinase (CK-MB) levels in their blood have significantly higher risk of early (first year) and late (3 to 5 years) morbidity and mortality. Perioperative and post-operative mortality and morbidity are related to iatrogenic ischemia-reperfusion injury during cardiac surgery, and to inadequate myocardial protection. In addition, in paediatric cardiac surgery more than 50% of infants have perioperative myocardial damage with a low cardiac output. For over two decades, a significant part of the iatrogenic injury has been linked to the type, composition and delivery of cardioplegia.

In 2000, about 64% of open-heart surgery operations performed were coronary artery bypass graft procedures, 24% were heart valve replacement or repair procedures, and about 12% were related to the repair of congenital heart defects. About 1.2% were neonatal/paediatric. The majority of open heart surgery operations (over 80%) require cardiopulmonary bypass and elective heart arrest using either a blood or crystalloid cardioplegia solution. During these procedures the heart may be arrested for 3 hours, but sometimes up to 4 to 6 hours. The amount of damage to the heart caused by 3-4 hours is such that the heart is increasingly less likely to recover function, and more likely than not recover after 4 hours arrest.

Cardioplegic compositions have been used to arrest or quieten the heart during surgery. Cardioplegic drugs are usually partially diluted and mixed with a carrier (e.g. ratio 4 blood:1 crystalloid), or used as a crystalloid alone. A small proportion of procedures are performed under what is called "miniplegia" or "microplegia" in which small amounts of the cardioplegic solution/drugs are mixed with large volumes of blood (e.g. ratio 66 blood:1 crystalloid). Miniplegia is delivered directly to the tissue of interest (eg the heart) rather than the larger amounts required to be delivered systemically. The objective has been to arrest the heart and create a "motionless, bloodless field" for the surgeon to operate and minimise damage to the tissue during the procedure (including the potentially substantial damage which can occur during reperfusion when the cardioplegia is removed and the heart reanimates). Dr. Melrose, in 1955, utilized the patient's own blood as the vehicle to administer potassium citrate into the aorta to arrest a heart. In 1976, Dr. Hearse described administering crystalloid cardioplegia. A few years later Buckberg and colleagues suggested using a patient's own blood as the major carrier because blood has an oxygen-carrying capacity, superior oncotic and buffering properties, and endogenous antioxidants. Whole blood cardioplegia has also been modified using larger volumes of blood and smaller titrations of potassium, hence the name "miniplegia". The term "Miniplegia" was coined by Menasche and colleagues in the early 1990s. Miniplegia (or Microplegia) provided oxygen-rich blood coupled with micro titrations of arrest and additives to achieve a quiescence of the heart and reduce ischemia-reperfusion injury.

Ischemic injury to a large extent is dependent upon the duration of the ischemic event, whether global or regional in nature. With ischemia being defined as the mismatch between oxygen supply (coronary blood flow and oxygen carrying capacity) and oxygen demand (determined by the wall stress, heart rate and contractility or inotropic state of the heart), the severity of ischemia is an important factor determining subsequent injury. The severity of ischemia can be offset, and even neutralized, by increased collateral blood flow. The basic premise of "miniplegia" is to minimize ischemia and therefore injury.

By definition, maintenance of cardiac aerobic metabolism during arrest requires oxygen supply to match oxygen demand. Consequently, where the oxygen demand has been drastically reduced by over 90% during adequate cardioplegic induction and maintenance of asystole, for the heart to maintain aerobic metabolism a number of factors or modalities must be met. These modalities can be summarized as follows: (i) oxygen must be present in sufficient quantities to match demand, and there is now convincing evidence that hematocrit should be at least equal to 24%; (ii) oxygen must be delivered at a sufficient flow rate to match demand; (iii) oxygen should be delivered in as near a continuous fashion as possible, without restricting surgeon's view, because it is consumed over time (no matter what the "safe" ischemic interval is in experimental models, it is virtually impossible to predict, in a given patient, the time point beyond which myocardial metabolism is going to shift from aerobic to anaerobic patterns as well as the extent and reversibility of tissue damage that may occur beyond this cut-off time mark); and (iv) oxygen must be delivered as uniformly as possible throughout the myocardium. When tight stenosis and furthermore, complete occlusions of the coronary arteries are present, there is now a convincing body of evidence that retrograde or, even better, a combined retrograde/antegrade approach are more effective in ensuring homogeneous distribution of cardioplegia than the antegrade route administration alone.

While early reperfusion, or restoration of the blood flow, remains the most effective means of salvaging the myocardium from acute ischaemia, the sudden influx of oxygen paradoxically may lead to necrosis, arrhythmias and death. The extent of "reperfusion injury" has been linked to a cascade of inflammatory reactions including the generation of cytokines, leukocytes, reactive oxygen species and free radicals. Reperfusion of ischaemic myocardium is necessary to salvage tissue from eventual death. However, reperfusion after even brief periods of ischaemia is associated with pathologic changes that represent either an acceleration of processes initiated during ischaemia per se, or new pathophysiological changes that were initiated after reperfusion. The degree and extent of reperfusion injury can be influenced by inflammatory responses in the myocardium. Ischaemia-reperfusion prompts a release of oxygen free radicals, cytokines and other pro-inflammatory mediators that activate both the neutrophils and the coronary vascular endothelium. The inflammatory process can lead to endothelial dysfunction, microvascular collapse and blood flow defects, myocardial infarction and apoptosis. Pharmacologic anti-inflammatory therapies targeting specific steps have been shown to decrease infarct size and myocardial injury.

Hypothermia has been an essential component of myocardial protection since the very beginning. The focus has always been on reducing metabolism to the lowest possible level during ischemic interval so that myocardial energy stores (adenosine tri-phosphate and glycogen) are maintained and tissue acidosis is avoided during this ischemic episode. However, many investigators have found that the level of myocardial recovery after crystalloid cardioplegia utilizing 10° C. or 25° C. was not significantly different. Until recently the major focus of myocardial protection has been that of preserving myocyte contractility to prevent pump failure which includes conserving cell energy by reducing metabolism to a low level which allows continued support of vital cell activities such as ion pumping to maintain internal milieu. Not only is there much interest in the current techniques involving cardiac and systemic temperature during cardioplegia, but also in the effect of cardioplegia on the endothelium and microvascular compartments. Thus, endothelium preservation may be as important as myocyte preservation.

Current techniques still result in a substantial number of patients suffering atrial fibrillation post-operatively. Patients typically require several days in intensive care following the operation, and take some time to return to lucidity and mobility. These reflect the damage, some of which is reversible, that results from current procedures and the need for improved techniques.

SUMMARY OF THE INVENTION

The invention is directed to reducing tissue, organ and cell damage resulting from periods of reduced activity, ie quiescence of cells, whether resulting from medical intervention or otherwise. Typically, it has application where cells are deliberately quietened for surgical purposes, such as induced cardiac arrest for cardiac surgery. The invention is described in this specification primarily with reference to the heart as an organ for which there is a critical commercial need for improved tissue maintenance. Medical intervention includes cardioplegia, ie medically induced arrest of the heart. However, the invention is not limited to cardiac tissue and is equally applicable and useful for other organs, including neuronal tissue and cells, renal tissue, lung tissue, muscle tissue etc. The invention also has application to protect an organ following non-medically induced periods of reduced activity, eg. trauma, shock, heart attack, stroke and like events.

The term "organ" is used herein in its broadest sense and refers to any part of the body exercising a specific function including tissues and cells or parts thereof, for example, cell lines or organelle preparations. Other examples include circulatory organs such as the heart, respiratory organs such as the lungs, urinary organs such as the kidneys or bladder, digestive organs such as the stomach, liver, pancreas or spleen, reproductive organs such as the scrotum, testis, ovaries or uterus, neurological organs such as the brain, germ cells such as spermatozoa or ovum and somatic cells such as skin cells, heart cells i.e., myocytes, nerve cells, brain cells or kidney cells.

The term "tissue" is used herein in its broadest sense and refers to any part of the body exercising a specific function including organs and cells or parts thereof, for example, cell lines or organelle preparations. Other examples include conduit vessels such as arteries or veins or circulatory organs such as the heart, respiratory organs such as the lungs, urinary organs such as the kidneys or bladder, digestive organs such as the stomach, liver, pancreas or spleen, reproductive organs such as the scrotum, testis, ovaries or uterus, neurological organs such as the brain, germ cells such as spermatozoa or ovum and somatic cells such as skin cells, heart cells (ie, myocytes), nerve cells, brain cells or kidney cells.

It will be understood that the term "comprises" or its grammatical variants as used in this specification and claims is equivalent to the term "includes" and is not to be taken as excluding the presence of other elements or features.

In one embodiment, the invention provides a method of reducing damage to a tissue, organ or cell from medically induced reduced activity (eg to facilitate surgical procedures), which consequently reduces risk or incidence of post-operative complications (such as atrial fibrillation after heart surgery). The method comprises administering a composition comprising a potassium channel opener/agonist and/or an adenosine receptor agonist (eg. adenosine) together with a local anaesthetic (eg. lignocaine) when reperfusing the organ. Preferably, a potassium channel opener/agonist or an adenosine receptor agonist is used.

In a preferred form, the composition is administered directly to the tissue, organ or cell. In another embodiment, the composition is administered substantially continuously (rather than as a bolus). In this context, "substantially continuously" permits minor interruptions to the administration.

Accordingly, in another embodiment, the invention provides a composition for reducing damage to tissue(s) and/or organ(s) comprising a potassium channel opener/agonist and/or an adenosine receptor agonist together with a local anaesthetic. The composition may further include other components as identified below. In some embodiments, the potassium channel opener/agonist and adenosine receptor agonist is replaced by another component such as a calcium channel agonist.

The invention also provides use of a composition comprising a potassium channel opener/agonist and/or an adenosine receptor agonist together with a local anaesthetic in the manufacture of a medicament for reducing damage to tissue(s) and/or organ(s), in particular for reducing post-operative atrial fibrillation after heart surgery.

In one embodiment, the organ is a heart. In this embodiment, the composition may be administered at about the time the cross-clamp is removed. The composition may also be administered during the procedure once the heart has been arrested, ie the cardioplegic composition has been administered.

Preferably, the composition includes magnesium cations. Magnesium sulphate is a suitable source for these.

Preferably, the composition is between 0° and 37° C. for administration. In some embodiments, temperatures of between about 4° and 15° C. are appropriate. In other embodiments, the composition is heated to between 20° and 37° C. before administration.

The invention also provides a method wherein the composition is administered when reperfusing the organ and/or wherein the composition is administered while perfusing the organ during a quiescent state. This is often called the "maintenance" phase of a surgical procedure.

In another embodiment, the composition is administered prior to the administration of the cardioplegia as a "preconditioning" step. The preconditioning may be effected by administration of the composition directly to the organ which is the subject of the procedure, or systemically to the subject. The preconditioning step has been observed to have a protective effect.

Accordingly, in one preferred form of the invention, a composition of the type described above is administered pre-induction of arrest, during maintenance and as part of the recovery phase of a surgical procedure.

In one embodiment, the invention provides a method of reducing post-operative fibrillation following a heart procedure comprising administering a composition comprising a potassium channel opener/agonist and/or an adenosine receptor agonist, together with a local anaesthetic. Preferably, the composition is administered during the recovery phase of the procedure.

The invention also provides use of a composition (especially in the preferred embodiments described below) for the methods described above. This uses of the composition extend to many therapeutic applications, including without limitation, cardiovascular diagnosis (including coronary angiography, myocardial scintigraphy, non-invasive diagnosis of dual AV nodal conduction), use in treatment of heart attack, resuscitation therapy, short-term and long-term storage of organs tissues or cells (including graft vessels), use before, prior to, during or following open-heart surgery, angioplasty and other therapeutic interventions.

In one embodiment, the composition comprises adenosine and lignocaine. In particular, the composition may include adenosine and lignocaine in the weight ratio of about 1:0.5 to 4, in particular 1:2.

Without being bound by any theory or mode of action, protection is thought to involve a multi-tiered system from modulating membrane excitability to a multitude of intracellular signalling pathways leading to (i) reduced ion imbalances, in particular sodium and calcium ion loading in the cells, (ii) improved atrial and ventricular matching of electrical conduction to metabolic demand, which may involve modulation of gap junction communication, (iii) vasodilation of coronary arteries and (ii) attenuation of the inflammatory response to injury Infusion of the composition during pre-treatment and ischaemia and reperfusion provides continuous protection from ischaemic tissue injury including protection from lethal arrhythmias. The protection from localised injury and inflammation can also be obtained when placing a stent into a vessel such as during angioplasty.

Local anaesthetic agents are drugs which are used to produce reversible loss of sensation in an area of the body. Many local anaesthetic agents consist of an aromatic ring linked by a carbonyl containing moiety through a carbon chain to a substituted amino group. In general there are 2 classes of local anaesthetics defined by their carbonyl-containing linkage group. The ester agents include cocaine, amethocaine, procaine and chloroprocaine, whereas the amides include prilocaine, mepivacaine, bupivacaine, mexiletine and lignocaine. At high concentrations, many drugs that are used for other purposes possess local anaesthetic properties. These include opioid analgesics, Beta-adrenoceptor antagonists, anticonvulsants (lamotrigine and lifarizine) and antihistamines. The local anaesthetic component of the composition according to the present invention may be selected from these classes, or derivatives thereof, or from drugs than may be used for other purposes. Preferably, the component possesses local anaesthetic properties also.

A suitable local anaesthetic is Lignocaine. In this specification Lignocaine and Lidocaine are used interchangeably. Lignocaine is preferred as it is capable of acting as a local anaesthetic probably by blocking sodium fast channels, depressing metabolic function, lowering free cytosolic calcium, protecting against enzyme release from cells, possibly protecting endothelial cells and protecting against myofilament damage. At lower therapeutic concentrations lignocaine normally has little effect on atrial tissue, and therefore is ineffective in treating atrial fibrillation, atrial flutter, and supraventricular tachycardias. Lignocaine is also a free radical scavenger, an antiarrhythmic and has anti-inflammatory and anti-hypercoagulable properties. It must also be appreciated that at non-anaesthetic therapeutic concentrations, local anaesthetics like lignocaine may not completely block the voltage-dependent sodium fast channels, but down-regulate channel activity and reduce sodium entry. As an anti-arrhythmic, lignocaine is believed to target small sodium currents that normally continue through phase 2 of the action potential and consequently shortens the action potential and the refractory period.

Lignocaine is a local anaesthetic which is believed to block sodium fast channels and has anti-arrhythmatic properties by reducing the magnitude of inward sodium current. In this specification, the terms "lidocaine" and "lignocaine" are used interchangeably. The accompanying shortening of the action potential is thought to directly reduce calcium entry into the cell via $Ca^{2+}$ selective channels and $Na^+/Ca^{2+}$ exchange. Recent reports also implicate lignocaine with the scavenging of free radicals such as hydroxyl and singlet oxygen in the heart during reperfusion. Examples of other suitable sodium channel blockers include venoms such as tetrodotoxin, and the drugs primaquine, QX, HNS-32 (CAS Registry #186086-10-2), NS-7, kappa-opioid receptor agonist U50 488, crobenetine, pilsicainide, phenytoin, tocainide, mexiletine, RS100642, riluzole, carbamazepine, flecainide, propafenone, amiodarone, sotalol, imipramine and moricizine, or any of derivatives thereof. Other suitable sodium channel blockers include: Vinpocetine (ethyl apovincaminate); and Beta-carboline derivative, nootropic beta-carboline (ambocarb, AMB).

The composition according to the invention includes a potassium channel opener. Potassium channel openers are agents which act on potassium channels to open them through a gating mechanism. This results in efflux of potassium across the membrane along its electrochemical gradient which is usually from inside to outside of the cell. Thus potassium channels are targets for the actions of transmitters, hormones, or drugs that modulate cellular function. It will be appreciated that the potassium channel openers include the potassium channel agonists which also stimulate the activity of the potassium channel with the same result. It will also be appreciated that there are diverse classes of compounds which open or modulate different potassium channels; for example, some channels are voltage dependent, some rectifier potassium channels are sensitive to ATP depletion, adenosine and opioids, others are activated by fatty acids, and other channels are modulated by ions such as sodium and calcium (ie. channels which respond to changes in cellular sodium and calcium). More recently, two pore potassium channels have been discovered and thought to function as background channels involved in the modulation of the resting membrane potential.

Potassium channel openers may be selected from the group consisting of: nicorandil, diazoxide, minoxidil, pinacidil, aprikalim, cromokulim and derivative U-89232, P-1075 (a selective plasma membrane KATP channel opener), emakalim, YM-934, (+)-7,8-dihydro-6, 6-dimethyl-7-hydroxy-8-(2-oxo-1-piperidinyl)-6H-pyrano[2,3-f]benz-2,1,3-oxadiazole (NIP-121), RO316930, RWJ29009, SDZ-PCO400, rimakalim, symakalim, YM099, 2-(7,8-dihydro-6, 6-dimethyl-6H[1,4]oxazino[2,3-f][2,1,3]benzoxadiazol-8-yl)pyridine N-oxide, 9-(3-cyanophenyl)-3,4,6,7,9,10-hexahydro-1,8-(2H,5H)-acridinedione (ZM244085), [(9R)-9-(4-fluoro-3-125iodophenyl)-2,3,5,9-tetrahydro-4H-pyrano[3,4-b]thieno[2,3-e]pyridin-8(7H)-one-1,1-dioxide] ([125I]A-312110), (−)-N-(2-ethoxyphenyl)-N'-(1,2,3-trimethylpropyl)-2-nitroethene-1,1-diamine (Bay X 9228), N-(4-benzoyl phenyl)-3,3,3-trifluro-2-hydroxy-2-methyl-propionamine (ZD6169), ZD6169 (KATP opener) and ZD0947 (KATP opener), WAY-133537 and a novel dihydropyridine potassium channel opener, A-278637. In addition, potassium channel openers can be selected from BK-activators (also called BK-openers or BK(Ca)-type potassium channel openers or large-conductance calcium-activated potassium channel openers) such as benzimidazolone derivatives NS004 (5-trifluoromethyl-1-(5-chloro-2-hydroxyphenyl)-1,3-dihydro-2H-benzimidazole-2-one), NS1619 (1,3-dihydro-1-[2-hydroxy-5-(trifluoromethyl)phenyl]-5-(trifluoromethyl)-2H-benzimidazol-2-one), NS1608 (N-(3-(trifluoromethyl)phenyl)-N'-(2-hydroxy-5-chlorophenyl)urea), BMS-204352, retigabine (also GABA agonist). There are also intermediate (eg. benzoxazoles, chlorzoxazone and zoxazolamine) and small-conductance calcium-activated potassium channel openers.

In addition, potassium channel openers may act as indirect calcium antagonists, ie they act to reduce calcium entry into the cell by shortening the cardiac action potential duration through the acceleration of phase 3 repolarisation, and thus shorten the plateau phase. Reduced calcium entry is thought to involve L-type calcium channels, but other calcium channels may also be involved.

Some embodiments of the invention utilise direct calcium antagonists, the principal action of which is to reduce calcium entry into the cell. These are selected from at least five major classes of calcium channel blockers as explained in more detail below. It will be appreciated that these calcium antagonists share some effects with potassium channel openers, particularly ATP-sensitive potassium channel openers, by inhibiting calcium entry into the cell.

Adenosine is particularly preferred as the potassium channel opener or agonist. Adenosine is capable of opening the potassium channel, hyperpolarising the cell, depressing metabolic function, possibly protecting endothelial cells, enhancing preconditioning of tissue and protecting from ischaemia or damage. Adenosine's actions are complex as the drug has many broad-spectrum properties. Adenosine has been shown to increase coronary blood flow, hyperpolarise the cell membrane, and protect during ischemia and reperfusion. Adenosine also acts as a 'early' and 'delayed' preconditioning 'trigger' or agent to protect the heart against ischaemic injury. Part of adenosine's cardioprotective properties are believed to be activation of one or more of the adenosine receptor subtypes (A1, A2a, A2b and A3). Much of adenosine's protection has been ascribed to A1 and A3 receptor activation and their associated transduction pathways leading to preconditioning, protection and preservation of cell integrity. It is also known that adenosine, by activating A1 receptors, is involved in slowing the sinoatrial nodal pacemaker rate (negative chronotropy), delaying atrioventricular (A-V) nodal impulse conduction (negative dromotropy), reduces atrial contractility (negative inotropy), and inhibits the effect of catecholamines (antiadrenergic effect). The A1-stimulated negative chronotropic, dromotropic and inotropic effects of adenosine are linked to the drug's action to reduce the activity of adenyl cyclase, to activate the inward rectifier potassium current ($I_{K\text{-}Ado}$), inhibition of phospholipid turnover, activation of ATP-sensitive K channels, inhibits effect of catecholamines on the L-type $Ca^{2+}$ current and activation of nitric oxide synthase in AV nodal cells. A3 receptors have also shown to have direct cardio-protective effects, and A2 receptors have potent vasodilatory and anti-inflammatory actions in response to injury. Adenosine is also an indirect calcium antagonist, vasodilator, anti-arrhythmic, antiadrenergic, free radical scavenger, arresting agent, anti-inflammatory agent (attenuates neutrophil activation), analgesic, metabolic agent and possible nitric oxide donor.

It will be appreciated that anti-adrenergics such as beta-blockers, for example, esmolol, atenolol, metoprolol and propranolol could be used instead of or in combination with the potassium channel opener to reduce calcium entry into the cell. Preferably, the beta-blocker is esmolol. Similarly, alpha(1)-adrenoceptor-antagonists such as prazosin, could be used instead of or in combination with the potassium channel opener to reduce calcium entry into the cell and therefore calcium loading.

In one aspect of the invention there is provided a composition for preconditioning, protecting and/or reducing damage to tissues during ischemia or reperfusion comprising delivery of an effective amount of:
an antiadrenergic; and
a local anaesthetic.

According to this aspect of the present invention there is also provided a composition including an effective amount of an antiadrenergic and a local anaesthetic.

Preferably, the antiadrenergic is a beta-blocker. Preferably the beta-blocker is esmolol.

Adenosine is also known to indirectly inhibit the sodium-calcium exchanger which would reduce cell sodium and calcium loading. It will be appreciated that inhibitors of the sodium-calcium exchanger would lead to reduced calcium entry and magnify the effect of adenosine. $Na^+/Ca^{2+}$ exchange inhibitors may include benzamyl, KB-R7943 (2-[4-(4-Nitrobenzyloxy)phenyl]ethyl]isothiourea mesylate) or SEA0400 (2-[4-[(2,5-difluorophenyl)methoxy]phenoxy]-5-ethoxyaniline).

Since one of adenosine's properties is to reduce calcium entry and sodium entry in the heart and coronary vascular cells, it will be further appreciated that a compound leading to reduced calcium and sodium entry (or reduce calcium oscillations in the cell) before, during and/or following treatment could be used instead of or in combination with adenosine to reduce calcium entry into the cell. Such compounds may be selected from calcium channel blockers from three different classes: 1,4-dihydropyridines (eg. nitrendipine), phenylalkylamines (eg. verapamil), and the benzothiazepines (e.g. diltiazem, nifedipine).

Calcium channel blockers are also called calcium antagonists or calcium blockers. They are often used clinically to decrease heart rate and contractility and relax blood vessels. They may be used to treat high blood pressure, angina or discomfort caused by ischaemia and some arrhythmias, and they share many effects with beta-blockers (see discussion above).

Five major classes of calcium channel blockers are known with diverse chemical structures: 1. Benzothiazepines: eg Diltiazem, 2. Dihydropyridines: eg nifedipine, Nicardipine, nimodipine and many others, 3. Phenylalkylamines: eg Verapamil, 4. Diarylaminopropylamine ethers: eg Bepridil, 5. Benzimidazole-substituted tetralines: eg Mibefradil.

The traditional calcium channel blockers bind to L-type calcium channels ("slow channels") which are abundant in cardiac and smooth muscle which helps explain why these drugs have selective effects on the cardiovascular system.

Different classes of L-type calcium channel blockers bind to different sites on the alpha1-subunit, the major channel-forming subunit (alpha2, beta, gamma, delta subunits are also present). Different sub-classes of L-type channel are present which may contribute to tissue selectivity. More recently, novel calcium channel blockers with different specificities have also been developed for example, Bepridil, is a drug with Na+ and K+ channel blocking activities in addition to L-type calcium channel blocking activities. Another example is Mibefradil, which has T-type calcium channel blocking activity as well as L-type calcium channel blocking activity.

Three common calcium channel blockers are diltiazem (Cardizem), verapamil (Calan) and Nifedipine (Procardia). Nifedipine and related dihydropyridines do not have significant direct effects on the atrioventricular conduction system or sinoatrial node at normal doses, and therefore do not have direct effects on conduction or automaticity. While other calcium channel blockers do have negative chronotropic/dromotropic effects (pacemaker activity/conduction velocity). For example, Verapamil (and to a lesser extent diltiazem) decreases the rate of recovery of the slow channel in AV conduction system and SA node, and therefore act directly to depress SA node pacemaker activity and slow conduction. These two drugs are frequency- and voltage-dependent, making them more effective in cells that are rapidly depolarizing. Verapamil is also contraindicated in combination with beta-blockers due to the possibility of AV block or severe depression of ventricular function. In addition, mibefradil has negative chronotropic and dromotropic effects. Calcium channel blockers (especially verapamil) may also be particularly effective in treating unstable angina if underlying mechanism involves vasospasm.

Omega conotoxin MVIIA (SNX-111) is an N type calcium channel blocker and is reported to be 100-1000 fold more potent than morphine as an analgesic but is not addictive. This conotoxin is being investigated to treat intractible pain. SNX-482 a further toxin from the venom of a carnivorous spider venom, blocks R-type calcium channels. The compound is isolated from the venom of the African tarantula, *Hysterocrates gigas*, and is the first R-type calcium channel blocker described. The R-type calcium channel is believed to play a role in the body's natural communication network where it contributes to the regulation of brain function. Other Calcium channel blockers from animal kingdom include Kurtoxin from South African Scorpion; SNX-482 from African Tarantula, Taicatoxin from the Australian Taipan snake, Agatoxin from the Funnel Web Spider, Atracotoxin from the Blue Mountains Funnel Web Spider, Conotoxin from the Marine Snail, HWTX-I from the Chinese bird spider, Grammotoxin SIA from the South American Rose Tarantula. This list also includes derivatives of these toxins that have a calcium antagonistic effect.

Direct ATP-sensitive potassium channel openers (eg nicorandil, aprikalem) or indirect ATP-sensitive potassium channel openers (eg adenosine, opioids) are also indirect calcium antagonists and reduce calcium entry into the tissue. One mechanism believed for ATP-sensitive potassium channel openers also acting as calcium antagonists is shortening of the cardiac action potential duration by accelerating phase 3 repolarisation and thus shortening the plateau phase. During the plateau phase the net influx of calcium may be balanced by the efflux of potassium through potassium channels. The enhanced phase 3 repolarisation may inhibit calcium entry into the cell by blocking or inhibiting L-type calcium channels and prevent calcium (and sodium) overload in the tissue cell.

Potential uses for the combinational therapy include cardioplegia, management of ischaemic syndromes without or without clot-busters, cardiac surgery (on and off-pump), arrhythmia management, coronary interventions (balloon and stent), preconditioning an organ, tissue or cell to ischaemic stress, longer-term organ or cell preservation, peri- and post-operative pain management, peri- and post operative anti-inflammatory treatments, peri- and post operative anti-clotting strategies, resuscitation therapies, cardiovascular diagnosis and other related therapeutic interventions. One potential use for the anti-clotting strategy may be in the treatment of deep vein thrombosis and similar disorders and complications associated with surgery such as vascular, hip, cardiac and general surgery.

Calcium channel blockers can be selected from nifedipine, nicardipine, nimodipine, nisoldipine, lercanidipine, telodipine, angizem, altiazem, bepridil, amlodipine, felodipine, isradipine and cavero and other racemic variations. In addition, it will be appreciated that calcium entry could be inhibited by other calcium blockers which could be used instead of or in combination with adenosine and include a number of venoms from marine or terrestrial animals such as the omega-conotoxin GVIA (from the snail *conus geographus*) which selectively blocks the N-type calcium channel or omega-agatoxin IIIA and IVA from the funnel web spider *Agelelnopsis aperta* which selectively blocks R- and P/Q-type calcium channels respectively. There are also mixed voltage-gated calcium and sodium channel blockers such as NS-7. to reduce calcium and sodium entry and thereby assist cardioprotection.

It will be appreciated that a calcium channel blocker could be used instead of or in combination with the a local anaesthetic.

Thus, in another aspect of the invention there is provided a composition for preconditioning, protecting and/or reducing damage to a tissue during ischemia or reperfusion comprising delivery of an effective amount of:

a calcium channel blocker; and potassium channel opener or adenosine receptor agonist.

According to this aspect of the invention there is also provided a composition including an effective amount of a calcium channel blocker and a local anaesthetic. Preferably the calcium channel blocker is nifedipine.

In another embodiment, the composition according to the invention further includes an additional potassium channel opener. Preferably the additional potassium channel opener is diazoxide. Diazoxide is believed to preserve ion and volume regulation, oxidative phosphorylation and mitochondrial membrane integrity (appears concentration dependent). Diazoxide also affords cardioprotection by reducing mitochondrial oxidant stress at reoxygenation. There is also some evidence that the protective effects of potassium channel openers are associated with modulation of reactive oxygen species generation in mitochondria.

The composition according to the invention includes an adenosine receptor agonist. It will be appreciated that the adenosine receptor agonists include compounds which act both directly and indirectly on the receptor resulting in activation of the receptor, or mimic the action of the receptor having the same net effect.

Suitable adenosine receptor agonists can be selected from: $N^6$-cyclopentyladenosine (CPA), N-ethylcarboxamido adenosine (NECA), 2[p-(2-carboxyethyl)phenethyl-amino-5'-N-ethylcarboxamido adenosine (CGS-21680), 2-chloro-adenosine, $N^6$-[2-(3,5-demethoxyphenyl)-2-(2-methoxyphenyl]ethyladenosine, 2-chloro-$N^6$-cyclopentyladenosine (CCPA), N-(4-aminobenzyl)-9-[5-(methylcarbonyl)-beta- D-robofuranosyl]-adenine (AB-MECA), ([IS-[1a,2b,3b,4a(S*)]]-4-[7-[[2-(3-chloro-2-thienyl)-1-methyl-propyl]amino]-3H-imidazole[4,5-b]pyridyl-3-yl]cyclopentane carboxamide (AMP579), $N^6$-(R)-phenylisopropyladenosine (R-PLA), aminophenylethyladenosine 9APNEA) and_clohexyladenosine (CHA). Others include full adenosine A1 receptor agonists such as N-[3-(R)-tetrahydrofuranyl]-6-aminopurine riboside (CVT-510), or partial agonists such as CVT-2759 and allosteric enhancers such as PD81723. Other agonists include N6-cyclopentyl-2-(3-phenylaminocarbonyltriazene-1-yl)adenosine (TCPA), a very selective agonist with high affinity for the human adenosine A1 receptor, and allosteric enhancers of A1 adenosine receptor includes the 2-amino-3-naphthoylthiophenes. CCPA is a particularly preferred adenosine receptor agonist. CCPA an A1 adenosine receptor agonist.

Thus, in another aspect, the invention provides a composition for preconditioning, protecting and/or reducing damage to a tissue during ischemia or reperfusion comprising an effective amount of:
  potassium channel opener or adenosine receptor agonist;
  local anaesthetic; and
  CCPA.

Opioids, also known or referred to as opioid agonists, are a group of drugs that inhibit opium (Gr opion, poppy juice) or morphine-like properties and are generally used clinically as moderate to strong analgesics, in particular, to manage pain, both peri- and post-operatively. Other pharmacological effects of opioids include drowsiness, respiratory depression, changes in mood and mental clouding without loss of consciousness. Opioids are also believed to be involved as part of the 'trigger' in the process of hibernation, a form of dormancy characterised by a fall in normal metabolic rate and normal core body temperature. In this hibernating state, tissues are better preserved against damage that may otherwise be caused by diminished oxygen or metabolic fuel supply, and also protected from ischemia reperfusion injury. There are three types of opioid peptides: enkephalin, endorphin and dynorphin.

Opioids act as agonists, Interacting with stereospecific and saturable binding sites, in the heart, brain and other tissues. Three main opioid receptors have been identified and cloned, namely mu, kappa, and delta receptors. All three receptors have consequently been classed in the G-protein coupled receptors family (which class includes adenosine and bradykinin receptors). Opioid receptors are further subtyped, for example, the delta receptor has two subtypes, delta-1 and delta-2.

Cardiovascular effects of opioids are directed within the intact body both centrally (ie, at the cardiovascular and respiratory centres of the hypothalamus and brainstem) and peripherally (ie, heart myocytes and both direct and indirect effects on the vasculature). For example, opioids have been shown to be involved in vasodilation. Some, of the action of opioids on the heart and cardiovascular system may involve direct opioid receptor mediated actions or indirect, dose dependent non-opioid receptor mediated actions, such as ion channel blockade which has been observed with antiarrhythmic actions of opioids, such as arylacetamide drugs. It is also known that the heart is capable of synthesising or producing the three types of opioid peptides, namely, enkephalin, endorphin and dynorphin. However, only the delta and kappa opioid receptors have been identified on ventricular myocytes.

Without being bound by any mode of action, opioids are considered to provide cardioprotective effects, by limiting ischaemic damage and reducing the incidence of arrhythmias, which are produced to counter-act high levels of damaging agents or compounds naturally released during ischemia. This may be mediated via the activation of ATP sensitive potassium channels in the sarcolemma and in the mitochondrial membrane and involved in the opening potassium channels. Further, it is also believed that the cardioprotective effects of opioids are mediated via the activation of ATP sensitive potassium channels In the sarcolemma and in the mitochondrial membrane. Thus it is believed that the opioid can be used in stead or in combination with the potassium channel opener or adenosine receptor agonist as they are also involved in indirectly opening potassium channels.

It will be appreciated that the opioids include compounds which act both directly and indirectly on opioid receptors. Opioids also include indirect dose dependent, non-opioid receptor mediated actions such as ion channel blockade which have been observed with the antiarrhythmic actions of opioids.

Thus, in another aspect of the invention there is provided a composition for preconditioning, protecting and/or reducing damage to an organ, tissue or cell during ischemia and/or reperfusion comprising delivery of an effective amount of:
  an opioid; and
  a local anaesthetic.

According to this aspect of the invention there is also provided a composition including an effective amount of opioid and a local anaesthetic. Preferably the opioid is selected from enkephalins, endorphins and dynorphins. Preferably, the opioid is an enkephalin which targets delta, kappa and/or mu receptors. More preferably the opioid is selected from delta-1-opioid receptor agonists and delta-2-opioid receptor agonists. D-Pen2, 5]enkephalin (DPDPE) is a particularly preferred Delta-1-Opioid receptor agonist.

In another embodiment of the present invention there is provided a composition according to the present invention, further including an effective amount of an antioxidant. Antioxidants are commonly enzymes or other organic substances that are capable of counteracting the damaging effects of oxidation in the tissue. The antioxidant component of the composition according to the present invention may be selected from one or more of the group consisting of: allopurinol, carnosine, histidine, Coenzyme Q 10, n-acetylcysteine, superoxide dismutase (SOD), glutathione reductase (GR), glutathione peroxidase (GP) modulators and regulators, catalase and the other metalloenzymes, NADPH and AND(P)H oxidase inhibitors, glutathione, U-74006F, vitamin E, Trolox (soluble form of vitamin E), other tocopherols (gamma and alpha, beta, delta), tocotrienols, ascorbic acid, Vitamin C, Beta-Carotene (plant form of vitamin A), selenium, Gamma Linoleic Acid (GLA), alpha-lipoic acid, uric acid (urate), curcumin, bilirubin, proanthocyanidins, epigallocatechin gallate, Lutein, lycopene, bioflavonoids, polyphenols, trolox(R), dimethyithiourea, tempol(R), carotenoids, coenzyme Q, melatonin, flavonoids, polyphenols, aminoindoles, probucol and nitecapone, 21-aminosteroids or lazaroids, sulphydryl-containing compounds (thiazolidine, Ebselen, dithiolethiones), and N-acetylcysteine. Other antioxidants include the ACE inhibitors (captopril, enalapril, lisinopril) which are used for the treatment of arterial hypertension and cardiac failure on patients with myocardial infarction. ACE inhibitors exert their beneficial effects on the reoxygenated myocardium by scavenging reactive oxygen species. Other antioxidants that could also be used include beta-mercaptopropionylglycine, 0-phenanthroline, dithiocarbamate, selegilize and desferrioxamine (Desferal), an iron chelator, has been used in experimental infarction models, where it exerted some level of antioxidant protection. Spin trapping agents such as 5'-5-dimethyl-1-pyrrolione-N-oxide (DMPO) and (a-4-pyridyl-1-oxide)-N-t-butylnitrone (POBN) also act as antioxidants. Other antioxidants include: nitrone radical scavenger alpha-phenyl-tert-N-butyl nitrone (PBN) and derivatives PBN (including disulphur derivatives); N-2-mercaptopropionyl glycine (MPG) a specific scavenger of the OH free radical; lipooxygenase inhibitor nordihydroguaretic acid (NDGA); Alpha Lipoic Acid; Chondroitin Sulfate; L-Cysteine; oxypurinol and Zinc.

Preferably, the antioxidant is allopurinol (1H-Pyrazolo[3,4-α]pyrimidine-4-ol). Allopurinol is a competitive inhibitor of the reactive oxygen species generating enzyme xanthine oxidase. Allopurinol's antioxidative properties may help preserve myocardial and endothelial functions by reducing oxidative stress, mitochondrial damage, apoptosis and cell death. In addition, protease inhibitors attenuate the systemic inflammatory response in patients undergoing cardiac surgery with cardiopulmonary bypass, and other patients where the inflammatory response has been heightened such as AIDS or in the treatment of chronic tendon injuries. Some broad spectrum protease inhibitors such as aprotinin also reduce blood loss and need for blood transfusions in surgical operations such as coronary bypass.

In another embodiment of the present invention there is provided a composition according to the present invention, further including an effective amount of a sodium hydrogen exchange inhibitor. The sodium hydrogen exchange inhibitor reduces sodium and calcium entering the cell. The sodium hydrogen exchange inhibitor may be selected from one or more of the group consisting of amiloride, cariporide, eniporide, triamterene and EMD 84021, EMD 94309, EMD 96785 and HOE 642 and T-162559 (inhibitors of the isoform 1 of the $Na^+/H^+$ exchanger). Preferably, the sodium hydrogen exchange inhibitor is amiloride. Amiloride inhibits the sodium proton exchanger ($Na^+/H^+$ exchanger, also often abbreviated NHE-1) and reduces calcium entering the cell.

During ischaemia excess cell protons (or hydrogen ions) are exchanged for sodium via the $Na^+/H^+$ exchanger.

Accordingly another aspect of the invention provides a composition for preconditioning, protecting and/or reducing damage to a tissue during ischemia or reperfusion comprising delivery of an effective amount of:
 a $Na^+/H^+$ exchange inhibitor; and
 a local anaesthetic.

Preferably the $Na^+/H^+$ exchange inhibitor is Amiloride.

In yet another embodiment of the present invention there is provided a composition according to the present invention, further including an effective amount of a source of magnesium in an amount for increasing the amount of magnesium in a cell in the tissue; and/or a source of calcium in an amount for increasing the amount of calcium in a cell in the tissue.

Elevated magnesium and low calcium has been associated with protection during ischaemia and reoxygenation of the organ. The action is believed due to decreased calcium loading. Preferably the magnesium is present at a concentration of between 0.5 mM to 20 mM, more preferably about 2.5 mM. Preferably the calcium present is at a concentration of between 0.1 mM to 2.5 mM, more preferably about 0.3 mM. In another aspect there is also provided a composition according to the invention further including an effective amount of elevated magnesium.

The composition according to the invention may also include an impermeant or a compound for minimizing or reducing the uptake of water by a cell in a tissue. Compounds for minimizing or reducing the uptake of water by a cell in a tissue are typically impermeants or receptor antagonists or agonists. A compound for minimizing or reducing the uptake of water by a cell in the tissue tends to control water shifts, ie, the shift of water between the extracellular and intracellular environments. Accordingly, these compounds are involved in the control or regulation of osmosis. One consequence is that a compound for minimizing or reducing the uptake of water by a cell in the tissue reduces cell swelling that is associated with Oedema, such as Oedema that can occur during ischemic injury.

An impermeant according to the present invention may be selected from one or more of the group consisting of: sucrose, pentastarch, hydroxyethyl starch, raffinose, mannitol, gluconate, lactobionate, and colloids. Colloids include albumin, hetastarch, polyethylene glycol (PEG), Dextran 40 and Dextran 60. Other compounds that could be selected for osmotic purposes include those from the major classes of osmolytes found in the animal kingdom including polyhydric alcohols (polyols) and sugars, other amino acids and amino-acid derivatives, and methylated ammonium and sulfonium compounds.

Cell swelling can also result from an inflammatory response which may be important during organ retrieval, preservation and surgical grafting. Substance P, an important pro-inflammatory neuropeptide is known to lead to cell oedema and therefore antagonists of substance P may reduce cell swelling. Indeed antagonists of substance P, (-specific neurokinin-1) receptor (NK-1) have been shown to reduce inflammatory liver damage, i.e., oedema formation, neutrophil infiltration, hepatocyte apoptosis, and necrosis. Two such NK-1 antagonists include CP-96,345 or [(2S,3S)-cis-2-(diphenylmethyl)-N-((2-methoxyphenyl)-methyl)-1-azabicyclo(2.2.2.)-octan-3-amine (CP-96,345)] and L-733,060 or [(2S,3-([3,5-bis(trifluoromethyl)phenyl]methoxy)-2-phenylpiperidine]. R116301 or [(2R-trans)-4-[1-[3,5-bis(trifluoromethyl)benzoyl]-2-(phenylmethyl)-4-piperidinyl]-N-(2,6-dimethylphenyl)-1-acetamide (S)-Hydroxybutanedioate] is another specific, active neurokinin-1 (NK(1)) receptor antagonist with subnanomolar affinity for the human NK(1) receptor (K(i): 0.45 nM) and over 200-fold selectivity toward NK(2) and NK(3) receptors. Antagonists of neurokinin receptors 2 (NK-2) that may also reduce cell swelling include SR48968 and NK-3 include SR142801 and SB-222200. Blockade of mitochondrial permeability transition and reducing the membrane potential of the inner mitochondrial membrane potential using cyclosporin A has also been shown to decrease ischemia-induced cell swelling in Isolated brain slices. In addition glutamate-receptor antagonists (AP5/CNQX) and reactive oxygen species scavengers (ascorbate, Trolox(R), dimethylthiourea, tempol(R)) also showed reduction of cell swelling. Thus, the compound for minimizing or reducing the uptake of water by a cell in a tissue can also be selected from any one of these compounds.

It will also be appreciated that the following energy substrates can also act as impermeants. Suitable energy substrate can be selected from one or more from the group consisting of: glucose and other sugars, pyruvate, lactate, glutamate, glutamine, aspartate, arginine, ectoine, taurine, N-acetyl-beta-lysine, alanine, proline and other amino acids and amino acid derivatives, trehalose, floridoside, glycerol and other polyhydric alcohols (polyols), sorbitol, myo-innositol, pinitol, insulin, alpha-keto glutarate, malate, succinate, triglycerides and derivatives, fatty acids and carnitine and derivatives.

Preferably the compound for minimizing or reducing the uptake of water by the cells in the tissue is sucrose. Sucrose reduces water shifts as an impermeant. Impermeant agents such as sucrose, lactobionate and raffinose are too large to enter the cells and hence remain in the extracellular spaces within the tissue and resulting osmotic forces prevent cell swelling that would otherwise damage the tissue, which would occur particularly during storage of the tissue.

Preferably, the concentration of the compound for minimizing or reducing the uptake of water by the cells in the tissue is between about 5 to 500 mM. Typically this is an effective amount for reducing the uptake of water by the cells in the tissue. More preferably, the concentration of the compound for reducing the uptake of water by the cells in the tissue is between about 20 and 100 mM. Even more preferably the concentration of the compound for reducing the uptake of water by the cells in the tissue is about 70 mM.

In another preferred embodiment of the present invention, there is provided a composition according to the present invention including an effective amount of:
 a potassium channel opener and/or adenosine receptor agonist; and
 a local anaesthetic,
and further including an effective amount of one or more components selected from:
 diazoxide;
 an opioid;
 an antioxidant;
 an anti-adrenergic;
 a sodium hydrogen exchange inhibitor;
 a calcium channel blocker;
 a source of magnesium; and
 a source of calcium.

The composition of the present invention is particularly useful in preconditioning, arresting, protecting and/or preserving the heart during open-heart surgery including heart transplants. Other applications include reducing heart damage before, during or following cardiovascular intervention which may include a heart attack, "beating heart" surgery, angioplasty or angiography. For example, the composition may be administered to subjects who have suffered or are developing a heart attack and used at the time of administration of blood clot-busting drugs such as streptokinase. As the clot is dissolved, the presence of the composition protects the heart from further injury, such as reperfusion injury.

The composition is particularly effective as a protectant in those portions of an organ, such as the heart, that have been starved of normal flow, nutrients and/or oxygen for different periods of time. For example, the composition may be used to treat ischaemia which could be pre-existing or induced by medical intervention.

In a preferred embodiment the composition according to the present invention is a cardioplegic and/or cardioprotectant composition.

According to another aspect of the present invention there is provided use of the composition according to the present invention in the manufacture of a medicament for preconditioning, protecting and/or preserving an organ.

In a preferred embodiment of this aspect of the present invention, it is preferred to aerate the composition with a source of oxygen before and/or during use. The source of oxygen may be an oxygen gas mixture where oxygen is the predominant component. The oxygen may be mixed with, for example $CO_2$. Preferably the oxygen gas mixture is 95% $O_2$ and 5% $CO_2$. It is considered that the oxygenation with the oxygen gas mixture maintains mitochondrial oxidation and this helps preserve the myocyte and endothelium of the tissue.

It will be appreciated that the amounts of active ingredients present in the composition will depend on the nature of the subject, the type of organ being arrested, protected and/or preserved and the proposed application. In the case of a human subject requiring heart arrest during open-heart surgery, the concentration of adenosine is preferably about 0.001 to about 2 mM, more preferably about 0.01 to about 10 mM, most preferably about 0.05 to about 5 mM and the concentration of lignocaine is preferably about 0.001 to about 2 mM, more preferably about 0.01 to about 10 mM, most preferably about 0.05 to about 5 mM.

For preconditioning, arresting, maintaining, reanimating or perfusing an organ, the form of the composition suitable for bathing the organ has a range of concentrations of adenosine from 0.001 mmols per liter to 0.10 mmols per liter for the maintenance and recovery phases, and from 0.10 to 10 mmols per liter for arresting a heart or other organ. As mentioned above, the concentration of lignocaine is often at a similar level, but both the absolute and relative amounts may vary. A ratio of adenosine:lignocaine of 1:3 is suitable for at least the maintenance and recovery phases. The composition may be delivered through one or more of a number of routes including intravenous, arterial, intraperitoneal, intracoronary (antegrade or retrograde), epidural and intra-brain routes. They could be administered either as a crystalloid alone or through various dilutions with a carrier such as blood ranging from 1:1 (1 blood:1 crystalloid dilutions), 1:4 (1 blood:4 crystalloid dilutions) to 64:1 (64 blood:1 crystalloid dilutions) or higher blood proportions.

The compositions are usually delivered at various flow rates. During the arrest phase, suitable flow rates are 100 to 1000 ml/min, preferably 200 to 300 ml/min and more preferably about 350 ml/min. During the maintenance and recovery phases, suitable flow rates are 100 to 1000 ml/min, preferably 200-300 ml/min, for retrograde delivery and 10 to 200 ml/min, preferably 50 to 100 ml/min, for antegrade delivery. The skilled person can adjust concentrations and flow rates to deliver the optimum amount of active (adenosine, lignocaine, etc.) to the organ as required.

In another preferred embodiment, the composition is mixed with a physiological carrier or crystalloid, such as Plasmalyte™ or Normosol™. In one preferred embodiment, where the procedure involves extra corporeal bypass, an additive cassette is added to the reperfusion solution comprising 4 mls of adenosine (being 12 mg at 3 mg per ml), 10 mls of magnesium sulphate (being about 5 g) and upon recovery 25 mg of lignocaine is added.

A preferred pharmaceutically acceptable carrier is a buffer having a pH of about 6 to about 9, preferably about 7, more preferably about 7.4 and/or low concentrations of potassium, for example, up to about 10 mM, more preferably about 2 to about 8 mM, most preferably about 4 to about 6 mM. Suitable buffers include Krebs-Henseleit which generally contains 10 mM glucose, 117 mM NaCl, 5.9 mM KCl, 25 mM NaHCO$_3$, 1.2 mM NaH$_2$PO$_4$, 1.12 mMCaCl$_2$ (free Ca$^{2+}$=1.07 mM) and 0.512 mM MgCl$_2$ (free Mg$^{2+}$=0.5 mM), St. Thomas No. 2 solution, Tyrodes solution which generally contains 10 mM glucose, 126 mM NaCl, 5.4 mM KCl, 1 mM CaCl$_2$, 1 mM MgCl$_2$, 0.33 mM NaH$_2$PO$_4$ and 10 mM HEPES (N-[2-hydroxyethyl]piperazine-N'-[2-ethane sulphonic acid], Fremes solution, Hartmanns solution which generally contains 129 NaCl, 5 mM KCl, 2 mM CaCl$_2$ and 29 mM lactate and Ringers-Lactate. One advantage of using low potassium is that it renders the present composition less injurious to the subject, in particular paediatric subjects such as neonates/infants. High potassium has been linked to an accumulation of calcium which may be associated with irregular heart beats during recovery, heart damage and cell swelling. Neonates/infants are even more susceptible than adults to high potassium damage during cardiac arrest. After surgery for defects a neonate/infant's heart may not return to normal for many days, sometimes requiring intensive therapy or life support. It is also advantageous to use carriers having low concentrations of magnesium, such as, for example up to about 2.5 mM, but it will be appreciated that higher concentrations of magnesium, for example up to about 20 mM, can be used if desired without substantially effecting the activity of the composition.

In a further preferred embodiment the present invention provides a pharmaceutical or veterinary composition which includes adenosine, lignocaine and a pharmaceutically acceptable carrier which contains less than about 10 mM potassium.

The composition may also advantageously be presented in the form of a kit in which the active ingredients are held separately for separate, sequential or simultaneous administration.

It will be appreciated that the composition of the present invention may also include and/or be used in combination with known medicaments depending on the proposed application. For instance, medicaments which substantially prevent the breakdown of adenosine in the blood such as nucleoside transport inhibitors, for example, dipyridamole could be used as additives in the composition of the present invention. The half life of adenosine in the blood is about 10 seconds so the presence of a medicament to substantially prevent its breakdown will maximise the effect of the composition of the present invention. Dipyridamole could advantageously be included in concentrations from about 0.1 nM to about 10 mM and has major advantages with respect to cardioprotection. Dipyridamole may supplement the actions of adenosine by inhibiting adenosine transport which increases vasodilation. This could be particularly important when the composition is administered intermittently.

The present invention also extends to a pharmaceutical or veterinary composition which includes the active ingredients and a pharmaceutically or veterinarily acceptable carrier, diluent, adjuvant and/or excipient.

This composition is ideally used with 100% miniplegia (or microplegia). Preferably, the perfusion method used follows a strict regimen of warm and cold cardioplegia delivery, and does not follow conventional myocardial protection dogma regarding time and volume constraints (that is; you may give as much volume as often as you want).

Surprisingly, an additional benefit of this method is improved urine production post-operatively by patients without the use of diuretics. Typically, diuretics are added to the patient's blood while they are supported by a heart-lung machine but it has been found that patients have less or no need for diuretics with the method of the invention. Similarly, it has been observed that patients' lucidity returns post-operatively more quickly with the method of the invention. Fewer days in an intensive care unit are also required— this is evidenced by the results of the example given below.

To illustrate the invention by way of example only, the following protocol was performed. This protocol utilises miniplegia as described above, where micro amounts are titrated directly onto the heart, using the patient's own oxygenated blood. The reference to a "setting" is a measure on the pump, such as a syringe pump, of the amount of substance being delivered directly to the organ, in this example a heart.

Two cassettes were prepared as follows.

(1) The Arrest Cassette:
1. 40 mls of undiluted Potassium having 80 mEq—thus, 2 mEq/ml
2. High Setting: 25 mEq's per liter
3. Low Setting: 10 mEq's per liter The potassium in item 1 above was the primary cardioplegic agent. High potassium is the most well known and used cardioplegic, despite its known disadvantages and deleterious side-effects. An alternative cardioplegic is disclosed in WO 00/56145 (GP Dobson) comprising a potassium channel opener/agonist and/or an adenosine receptor agonist (eg. adenosine) together with a local anaesthetic (eg. lignocaine) in mM amounts. The contents of this specification are incorporated herein by reference in entirety. Although not exemplified here, the high potassium cardioplegic of item 1 above could be replaced by such a cardioplegic.

(2) The Additive Cassette:
1. 4 ml Adenosine having 12 mg—thus, 3 mg/ml
2. 10 mls Magnesium Sulfate=5 g (or a vial of $MgSO_4$ to equal 5 g)
3. 30 mls—whatever crystalloid prime is in a pump can be used (e.g. L/R, Plasmalyte™, Normosol™)
4. Total Volume in Additive Cassette: 44 mls
5. Additive Setting: 10 mls per liter This cassette is suitable for machines which support 50 ml cassettes.

Lignocaine is added to this cassette as described below to deliver the improved results. Lignocaine is added at a concentration of 0.1 to 10 times that of adenosine, preferably 0.5 to 2 times.

The data below is from experiments where no lignocaine was not added to this cassette until the recovery phase shortly before cross-clamp removal. However, in another embodiment of the invention, lignocaine is added to this cassette from its first use so that a combination of adenosine and lignocaine is administered during the maintenance or quiescent phase of a procedure. It is found that this further improves the prospects of heart recovery and/or reduced post-operative complications.

The procedure used to administer the composition in this example was as follows, with an overall objective of creating aerobic arrest, not ischemic arrest.

1. Upon heparinization, fill the ice reservoir to the top with ice. Reservoir need not be filled again unless x-clamp time exceeds 3 hours. Delivery temp will be about 12° C. Towards the last third of the x-clamp period, some metabolism of oxygen rich blood should occur.
2. Temperature setting is for warm induction: Warm (37° C.)
3. High setting for arrest: 25 mEq/liter of the hyperkalemic Arrest cassette induces a rapid arrest
4. Setting for Additive: 10 ml/liter before cross-clamp Upon Application of Cross-Clamp:
1. Increase flow for antegrade quickly to 500 mls then immediately back down to 320 to 350 mls/min so as to ensure closure of the aortic valve.
2. Give 700 mls warm antegrade. Once quiescence achieved, give 300 mls more and then switch to low K+ setting (ie 10 ml/liter).
3. Give 700 mls warm retrograde.

4. Switch water temp to cold. Administer cold retrograde, for as long as possible. Lower arrest setting empirically the longer flow continues.
5. Lower additive setting to 2 ml/liter. Most preparation of the heart has occurred.
6. If you are doing a CABG and distals are performed first: after the first graft, hook up the graft to the pump via multi-catheter lines. The flow is then increased very slowly to achieve a pressure of 150 Torr and the flow is noted, which is useful information for the surgeon. This will accomplish several things:
    controlled mechanical device to determine patency of the graft utilizing the gold standard of pressure to flow ratio;
    surgeon has a means to check hemostasis of the anastomotic site; and
    capability to deliver antegrade to the target site and retrograde simultaneously if desired.
7. If the procedure involves work on a valve and coronaries, perform the coronaries first. This way a sick heart is provided with the nutrients it needs while the valve is being worked on.
8. Monitor K+ according to usual SOP and adjust potassium concentration to meet desired level.

When approaching the last 10 minutes of x-clamp, preparations are made for the warm shot. These include:
1. Water setting: Warm (37 degrees)
2. Arrest setting: 0—to wash out the K+ and other metabolites
3. 25 mg. Lignocaine is injected into Additive bag (in this embodiment being described, it has not been added earlier) to accomplish target delivery of the prophylactic antiarrhythmic composition—typically there is about 18-35 ml left in the Additive bag at this point depending on the length of time for the procedure, which provides a lignocaine concentration of about 1 mg/ml.
4. Additive setting: 15 to 18—the goal is to empty the Additive bag prior to removal of cross-clamp.

For warm shot: usually started 5 to 10 minutes prior to x-clamp removal
1. Start retrograde warm. Zero potassium, additive setting at 15. Make sure retrograde pressure is maintained at highest level (35 to 40 Torr)
2. When electrical activity begins, continue retrograde for another minute.
3. Switch to antegrade for 2 to 3 minutes (when not obscuring surgeons' vision). This will facilitate de-airing grafts, allowing the right side of the heart to be perfused and, usually, will achieve a stable heart rate.
4. Switch back to retrograde for duration of x-clamp.
5. If additive setting runs out, continue with pure warm blood through x-clamp removal.

With microplegic techniques, the more volume you give, the better the heart likes it as it is aerobic arrest. In many instances, if administered properly, the oxygen supply/demand ratio is reversed. Administration of over 1 and up to 6 liters is associated with the greatest reduction in postoperative fibrillation.

The clinical results attained with warm blood cardioplegia have suggested that earlier observations on impairment of some cell functions by hypothermia may be more relevant than previously thought. These include reduced:
1. Membrane stability
2. Ability to utilize glucose and fatty acids
3. Mitochondrial generation of adenosine tri-phosphate leading to depressed Cell membrane function
4. Activity of adenosine tri-phosphatase system, leading to impaired cell volume regulation
5. Decreased ability of the sarcoplasmic reticulum to bind calcium
6. Mitochondrial state respiration and activity of citrate synthetase
7. Control of intracellular pH
8. Activity of the sarcoplasmic reticulum with regard to calcium uptake Coupling warm induction with cold maintenance and warm shot towards the end of cross clamp provides superior results. Warm induction, especially with the addition of adenosine (a very powerful vasodilator, among other functions), opens up all the collaterals and provides the necessary conduit for arrest and additives to reach the myocyte and endothelium. With cold induction comes constriction and the inability to globally distribute cardioplegia down to the myocyte and endothelium.

Cold maintenance provides a reduction in metabolic uptake with the slow increase in temperature occurring during the natural course of cross clamp due to ice melting. Average temperature will drift to around 12 to 14° C. The warm shot at the end is a most important aspect of myocardial protection. By allowing the heart to experience warm blood (32 to 37° C.) as long as is possible, can mean the difference in regaining most of the heart's functional recovery as opposed to a flaccid, lifeless heart, requiring inotropes and electrical support. There is also evidence that subjecting a cold, flaccid, non-beating heart to the trauma of high flow warm blood, such as experienced when the cross clamp is removed, sets the heart up for sure fire reperfusion injury.

Over the course of the last 30 years, surgeons and perfusionists have refined their operative techniques, allowing them to "customize" how they approach each patient's particular needs and demands. The only area that has essentially remained a "cookie cutter" approach has been myocardial protection; essentially "one size fits all". Without being bound by any particular theory or mode of action, it is believed that the method of this preferred embodiment is more sensitive to not over-hemodiluting the patient and thus results in improved outcomes.

In one experiment, 2688 patients undergoing cardiac surgery using cardioplegia were assessed at 6 different hospitals using different surgeons and their different techniques to assess for variability in this delicate environment. All patients were treated with a standard hyperkalemic cardioplegic solution to induce arrest. Of the patients, 1279 were in the group subjected to typical standard crystalloid-cardioplegic protocol ("Standard"). 1409 were subjected to a microplegia protocol (ie one using minimal amounts of cardioplegic directly administered to the heart) using the same hyperkalemic cardioplegic and with a warm ALM Additive cassette as described above, ie having a composition according to the invention. The invention is not specific or limited to this form of cardioplegia, but it forms application of the method of the invention and is discussed here to assess and illustrate the effect of the invention.

The Additive cassette was used as described above, such that during the recovery phase it contained Adenosine, Lignocaine and Magnesium (hence the label "ALM"). The method of the invention is referred to as "ALM" as a convenient abbreviation only. ALM was administered at cross-clamp removal in accordance with the protocol described above.

Table 1 sets out the characteristics of the 2688 patients and Table 2 sets out the occurrence of different postoperative complications measured.

TABLE 1

| Patient Groups | | |
|---|---|---|
| | Standard | ALM |
| Number of Patients | 1279 | 1409 |
| Age (Years) | 62 ± 10 | 65.7 ± 10 |
| Weight (kg) | 89 ± 16 | 79.5 ± 16 |
| Height (cm) | 174 ± 9 | 168 ± 10 |
| Body mass index | 30 ± 5 | 29 ± 5 |
| Male (%) | 53 | 60 |
| Peripheral vascular disease (%) | 18 | 21 |
| Diabetes mellitus (%) | 36 | 35 |
| Emergency surgery (%) | 8 | 10 |
| Extra corporeal bypass time (min) | 87 ± 29 | 110 ± 37 |

In Table 2, the clinical outcomes are tabulated for the patients identified in Table 1. The third column represents the ALM proportion of patients as a percentage of the proportion of standard cardioplegia patients for each outcome (ie second column as a percentage of the first column). All of the outcomes in the left column are negative outcomes, and thus their minimisation is desired.

TABLE 2

| Clinical Observations | | | |
|---|---|---|---|
| | Standard | ALM | ALM as % of standard |
| Intra-operative inotropes (%) | 93% | 13% | (14%) |
| Intra-operative pacing (%) | 86% | 33% | (38%) |
| Intra-operative transfusions(%) | 43% | 24% | (56%) |
| Length of Stay post-op (days) | 7 | 6 | (79%) |
| Post-op atrial fib. (%) | 34% | 3% | (9%) |

It can be seen that there was a substantial reduction in complications following the above protocol, especially in post-operative atrial fibrillation and the need for intraoperative inotropes. In particular, the reductions in these negative outcomes are: 86% reduction of intraoperative inotropes; 64% reduction in intraoperative pacing; 44% reduction in intraoperative transfusions; 21% reduction in length of stay post-operative days and 91% reduction in post-operative atrial fibrillation.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method of reducing damage to a tissue, organ or cell resulting from cardioplegia comprising administering an additive composition comprising a potassium channel opener/agonist and/or an adenosine receptor agonist, together with a local anaesthetic and magnesium cations wherein the composition is administered when reperfusing the organ during the recovery phase of a surgical procedure.

2. A method according to claim 1, wherein the composition includes magnesium cations in an amount of from about 0.5 mM to about 20 mM.

3. A method according to claim 1, wherein the composition is heated to a temperature of from about 32° C. to about 37° C. before administration.

4. A method according to claim 1, further comprising administering the additive composition while perfusing the organ during a quiescent state.

5. A method according to claim 1, wherein the tissue, cell or organ is a heart.

6. A method according to claim 1, wherein the composition comprises a potassium concentration of less than about 10 mM.

7. A method according to claim 1, wherein the potassium channel opener/agonist is adenosine and the local anaesthetic is lignocaine.

8. A method according to claim 1, wherein the additive composition comprises adenosine, magnesium cations and lignocaine.

9. A method according to claim 1, wherein the damage to a tissue organ, or cell comprises post-operative fibrillation that occurs following a heart procedure.

10. A method according to claim 1, further comprising reanimating the tissue, organ or cell.

11. A method according to claim 1, wherein the composition further comprises an antioxidant.

12. A method according to claim 11, wherein the antioxidant is selected from allopurinol, carnosine, histidine, Coenzyme Q 10, superoxide dismutase, glutathione reductase, glutathione peroxidase modulators and regulators, catalase and metalloenzymes, NADPH and NADPH oxidase inhibitors, glutathione, U-74006F, Trolox, gamma tocopherols, alpha tocopherols, beta tocopherols, delta tocopherols, tocotrienols, ascorbic acid, Beta-Carotene, selenium, Gamma Linoleic Acid1, alpha-lipoic acid, uric acid, curcumin, bilirubin, proanthocyanidins, epigallocatechin gallate, Lutein, lycopene, bioflavonoids, dimethylthiourea, tempol, carotenoids, coenzyme Q, melatonin, flavonoids, polyphenols, aminoindoles, probucol, nitecapone, 21-aminosteroids, lazaroids, thiazolidine, Ebselen, dithiolethiones, and N-acetylcysteine.

13. A method according to claim 12, wherein the antioxidant is melatonin.

14. A method according to claim 1, wherein the composition further comprises an impermeant.

15. A method according to claim 14, wherein the impermeant is selected from glucose, sugars, pyruvate, lactate, glutamate, glutamine, aspartate, arginine, ectoine, taurine, N-acetyl-beta-lysine, alanine, proline, amino acids, and amino acid derivatives, trehalose, floridoside, glycerol, polyhydric alcohols (polyols), sorbitol, myo-innositol, pinitol, insulin, alpha-keto glutarate, malate, succinate, triglycerides and derivatives, fatty acids and carnitine and derivatives.

16. A method according to claim 15, wherein the impermeant is insulin.

* * * * *